(12) United States Patent
Han et al.

(10) Patent No.: US 9,640,365 B2
(45) Date of Patent: May 2, 2017

(54) METHOD FOR DETERMINING 3D PRIMITIVE RECIPROCAL BASIS OF UNKNOWN CRYSTAL BASED ON SINGLE EBSD PATTERN

(71) Applicant: East China Jiaotong University, Nanchang, Jiangxi (CN)

(72) Inventors: Ming Han, Jiangxi (CN); Lili Li, Jiangxi (CN); Guangyao Xiong, Jiangxi (CN); Honglin Luo, Jiangxi (CN); Yizao Wan, Jiangxi (CN)

(73) Assignee: East China Jiaotong University, Nanchang, Jiangxi (CN)

(*) Notice: Subject to any disclaimer, the term of this patent is extended or adjusted under 35 U.S.C. 154(b) by 0 days.

(21) Appl. No.: 14/994,140

(22) Filed: Jan. 13, 2016

(65) Prior Publication Data

US 2016/0238545 A1 Aug. 18, 2016

(30) Foreign Application Priority Data

Aug. 3, 2015 (CN) .......................... 2015 1 0479294

(51) Int. Cl.
*G01N 23/203* (2006.01)
*H01J 37/244* (2006.01)

(52) U.S. Cl.
CPC .......... *H01J 37/244* (2013.01); *G01N 23/203* (2013.01); *H01J 2237/2813* (2013.01)

(58) Field of Classification Search
CPC ... G01N 23/203; G01N 23/2058; H01J 37/28; H01J 37/244; H01J 2237/2813
See application file for complete search history.

(56) References Cited

U.S. PATENT DOCUMENTS

| | | | | |
|---|---|---|---|---|
| 5,557,104 A | * | 9/1996 | Field | G01N 23/203 250/306 |
| 6,326,619 B1 | * | 12/2001 | Michael | H01J 37/2955 250/307 |
| 2010/0108882 A1 | * | 5/2010 | Zewail | H01J 37/22 250/307 |

* cited by examiner

*Primary Examiner* — Nicole Ippolito
*Assistant Examiner* — Sean Luck

(57) ABSTRACT

A method for determining 3D primitive reciprocal basis of an unknown crystal based on a single EBSD pattern includes steps of geometrically correcting all visible Kikuchi bands with the pattern center and the detector distance used for obtaining corresponding reciprocal vectors, and determining components of the corresponding reciprocal vectors in a 3D reciprocal Cartesian coordinate system, so as to obtain a 3D primitive reciprocal basis. The method given in the present invention is able to effectively exclude fake primitive cells; correctly identify the volume of a primitive cell even though the presence of obvious errors in the width of the Kikuchi bands; and successfully determine a 3D primitive reciprocal basis of unknown crystals based on a single EBSD pattern.

4 Claims, 2 Drawing Sheets

METHOD FOR DETERMINING 3D PRIMITIVE RECIPROCAL BASIS OF UNKNOWN CRYSTAL BASED ON SINGLE EBSD PATTERN

CROSS REFERENCE OF RELATED APPLICATION

The present invention claims priority under 35 U.S.C. 119(a-d) to CN 201510479294.5, filed Aug. 3, 2015.

BACKGROUND OF THE PRESENT INVENTION

Field of Invention

The present invention relates to a technical field of materials microstructure characterization and crystal structure analysis, and more particularly to a method for determining a primitive reciprocal basis of unknown crystals based on single EBSD pattern.

Description of Related Arts

Electron backscatter diffraction (EBSD) is an important complement to scanning electron microscope (SEM), which has been widely used in crystal orientation analysis of materials in the past 20 years. With this technique, EBSD pattern of crystalline samples is collected on the SEM. An EBSD pattern provides a variety of crystallographic information. Usually, an EBSD pattern comprises dozens of Kikuchi bands. The Kikuchi band width is related to interplanar spacing of a characterized crystal. The Length and direction of reciprocal vectors of the crystal are able to be identified according to the width and azimuth of the Kikuchi bands. The Kikuchi bands intersect each other to form Kikuchi poles, wherein each Kikuchi pole is equivalent to a 2D reciprocal plane. An EBSD pattern generally comprises over a hundred of Kikuchi poles, which are equivalent to over a hundred of 2D reciprocal planes of the crystal. The above diffraction information is applicable to analysis of unknown crystal Bravais lattices (reference: L. L. Li and M. Han. Determining the Bravais lattice using a single electron backscatter diffraction pattern. *J. Appl. Cryst.* 48(2015):107-115).

The conventional methods for determining unknown crystal lattices are mainly X-ray diffraction (XRD) and selected-area electron diffraction (SAED). These classic methods have their own advantages and disadvantages. For the former one, analysis of cell parameters is highly accurate, and atomic coordinates inside the cell is able to be further accurately positioned according to diffraction intensity. However, microstructure morphology of the sample is not able to be real-time observed, and the sample is usually required to be a single phase. For the latter one, users are allowed to real-time observe the microstructure of the sample through a transmission electron microscope, and electron diffraction is provided to interested areas, so as to analyze crystallographic information while observe microstructure morphology, wherein that is the biggest advantage of SAED. The disadvantage of the latter is that the sample is difficult to prepare. The EBSD technique allows the users to directly characterize the microstructure morphology of the materials through the SEM, which keeps the advantage of the SAED. More importantly, because of using the SEM, sample preparation is greatly simplified. Determining 3D primitive reciprocal basis based on single EBSD pattern is conducive to reconstructing unknown lattice of bulk crystals, which is a novel application of EBSD technique.

Conventionally, the applicant disclosed analysis of Bravais lattice of unknown crystals based on EBSD patterns in references comprising: 3*D reconstruction for Bravais lattice of unknown crystals using EBSD pattern. Journal of Chinese Electron Microscopy Society*, December 2008, Vol. 27, No. 6; 3*D reconstruction for Bravais lattice of hexagonal crystal using single EBSD pattern. Journal of Chinese Electron Microscopy Society*, Aug. 2010, Vol. 29, No. 4; *Reconstruction for* 3*D primitive reciprocal cell of crystals using EBSD pattern. Paper collection of the second National Symposium on electron backscatter diffraction (EBSD) technology and application, the Sixth National Symposium on science and technology*, Dec. 31, 2007; and Chinese patent application No. 200810237624.X, Method for determining unknown crystal Bravais lattice using electron backscatter diffraction.

According to the above references, the applicant is the first to disclose geometrically determining Bravais lattices of unknown crystals based on single EBSD pattern, which means using a large amount of 2D reciprocal plane information, 3D reconstruction for reciprocal lattice, and reciprocal-direct space transformation. During reconstruction of Bravais lattice of unknown crystals, selection of a set of 3D primitive basis is a key point. For 3D lattice reconstruction, cell selection is not unique, which may comprise primitive cell and non-primitive cell. The primitive cells are only of one lattice point. Theoretically, all primitive cells for a given crystal have the same volume, moreover, primitive cell is always of the smallest volume in all cells, and the volume of the non-primitive cells should be integral multiple of the smallest one. However, because edge contrast of the Kikuchi bands in EBSD patterns is usually ambiguous, the measured error of the Kikuchi band width is large, which is up to 20% (reference: D. J. Dingley and S. I. Wright. Determination of crystal phase from an electron backscatter diffraction pattern. *J. Appl. Cryst.* 42(2009):234-241). In this case, cell volumes appear to continuously change. More critically, because of the deviation of the Kikuchi band trace line, fake cell volumes usually occur. Correct identification of a 3D primitive basis is a premise of determining Bravais lattice of unknown crystals. The present invention takes full advantage of the characteristic that there is a variety of crystallographic information in single EBSD pattern, and provides a method for correctly selecting a 3D primitive reciprocal basis from a single EBSD pattern.

For shortcomings of the conventional technique, the present invention is provided.

SUMMARY OF THE PRESENT INVENTION

For the shortcoming of the larger measured errors obtained from EBSD patterns, the present invention provides a method for determining a 3D primitive reciprocal basis based on single EBSD pattern of an unknown crystal.

Accordingly, the present invention provides a method for determining a 3D primitive reciprocal basis of unknown crystals based on an EBSD pattern, comprising steps of:

1) collecting an electron backscatter diffraction (EBSD) pattern of a crystalline sample with a scanning electron microscope (SEM), recording the pattern center (PC), the detector distance (DD), and the accelerating voltage used;

2) identifying edges at the narrowest width of each visible Kikuchi band on the EBSD pattern, determining central line of the Kikuchi bands on the EBSD pattern; wherein in the step 2), firstly determine the central line of the Kikuchi bands, then match the edges at the narrowest width of the Kikuchi bands with a pair of symmetrical parallel lines, so as to represent the width of the Kikuchi bands; or matching the edges at the narrowest location of the Kikuchi bands with two parallel lines, representing the width of the Kikuchi bands with the interval between the parallel lines, and representing the central line of the Kikuchi bands with the bisector of the parallel lines;

3) geometrically correcting the Kikuchi bands according to the PC and the DD, obtaining reciprocal vectors corresponding to the Kikuchi bands, and determining components of the reciprocal vectors in a 3D reciprocal Cartesian coordinate system;

wherein the step 3) specifically comprises sub-steps of:

3-1) calculating L according to the DD and the EBSD pattern width, wherein

L=(EBSD pattern width)×DD, wherein the L is a distance from the signal source to the PC of the EBSD pattern;

3-2) determining a position of the signal source with the PC and the L;

3-3) determining the angle $2\theta_i$ between planes $M_i$ and $N_i$ according to the position of the signal source and the parallel lines at the narrowest width of the Kikuchi bands, wherein after geometric correction, the width of the Kikuchi bands is $w_i=2 L \tan(\theta_i)$, the length of the reciprocal vectors is $$H_i = \frac{2}{\lambda}\tan(\theta_i);$$

and 3-4) determining the trace line of the Kikuchi bands with the intersection line formed by a bisector of planes $M_i$ and $N_i$ and the EBSD pattern plane;

4) selecting all possible three non-coplanar vectors in the reciprocal vectors, calculating the volumes of parallelepipeds defined by the non-coplanar reciprocal vectors, sequencing them from the smallest volume to the largest volume, and simultaneously recording the corresponding three non-coplanar reciprocal vectors forming the parallelepipeds;

5) circulating the sequenced volumes;

6) assigning the current volume to be variable V, wherein the three corresponding non-coplanar reciprocal vectors are respectively set to be a, b, and c, firstly calculating the parallelepiped volumes $V_{ab}$ formed by the a, b, and another reciprocal vector excluding the a, b, and c, then calculating $V_{ab}/V$, taking the nearest integers I; if one of the integers I equals to 2, jumping into step 7); otherwise, circulating to the next volume and repeating the step 6);

7) firstly calculating the parallelepiped volumes $V_{bc}$ formed by b, c, and another reciprocal vector excluding the a, b, and c, then calculating $V_{bc}/V$, taking the nearest integers J; if one of the integers J equals to 2, jumping into step 8); otherwise, circulating to the next volume and repeating the step 6);

8) firstly calculating the parallelepiped volumes $V_{ca}$ formed by c, a, and another reciprocal vector excluding the a, b, and c, then calculating $V_{ca}/V$, taking the nearest integers K; if one of the integers K equals to 2, jumping into step 9); otherwise, circulating to the next volume and repeating the step 6); and 9) determining the three non-coplanar reciprocal vectors corresponding to the current volume as a 3D primitive reciprocal basis.

Beneficial effects of the present invention are as follows.

Applying a single EBSD pattern to determine unknown Bravais lattices of the characterized crystal is a novel application of EBSD technique (reference: L. L. Li and M. Han. EBSDL: a computer program for determining an unknown Bravais lattice using a single electron backscatter diffraction pattern. J. Appl. Cryst. 47(2014):1466-1468). Because of the obvious errors in the original data obtained from EBSD patterns, the calculated cell volumes appear no longer to be discrete values, and the inherent multiple relationship between non-primitive cell volumes and primitive cell volume is not distinctive. Therefore, determining a set of 3D primitive reciprocal basis of an unknown crystal based on single EBSD pattern is still a challenge work. The conventional methods are disclosed in references comprising D. J. Dingley and S. I. Wright. Determination of crystal phase from an electron backscatter diffraction pattern. J. Appl. Cryst. 42(2009):234-241; and L. L. Li and M. Han. Determining the Bravais lattice using a single electron backscatter diffraction pattern. J. Appl. Cryst. 48(2015):107-115. The former relies on symmetry of the characterized crystal, which is clearly only applicable to high symmetry crystals, and is not suitable for low symmetry crystals. The latter uses a triple-circle test method for selecting a set of 3D primitive reciprocal basis, wherein each basis vector is assigned all over the reciprocal vectors and followed by indexing other reciprocal vectors according to the geometric relationships of the vectors on the reciprocal planes. Apparently, the result of selecting the basis depends strongly on the geometric relationships of the reciprocal vectors. Moreover, it needs a large amount of calculation. In addition, due to the obvious errors in the reciprocal vectors obtained from EBSD patterns, wrong indexing of the relative coordinates of the reciprocal vectors with respect to the basis often occurs. As a result, the published method is not able to effectively exclude some fake cell volumes caused by the obvious errors. For the disadvantage that the original data obtained from EBSD patterns are always of obvious errors, a new method for determining a 3D primitive reciprocal basis of an unknown crystal based on single EBSD pattern is provided. With the method of the present invention, fake primitive cells can be effectively excluded. Even though the volume of the cells appears to be continuously changing, the volume of the primitive cells is still correctly identified, and a 3D primitive reciprocal basis can be correctly determined.

BRIEF DESCRIPTION OF THE DRAWINGS

These and other objectives, features, and advantages of the present invention will become apparent from the accompanying drawings and the following detailed description. The drawings are shown and described for the purposes of further illustrating and being a part of the present invention. Embodiment of the present invention as shown in the drawings and described below is exemplary only and not intended to be limiting.

DETAILED DESCRIPTION OF THE PREFERRED EMBODIMENT

To more clearly understand the above objects, characteristics and advantages, the present invention is further described in detail combined with the drawings and the embodiments.

Figure 1:
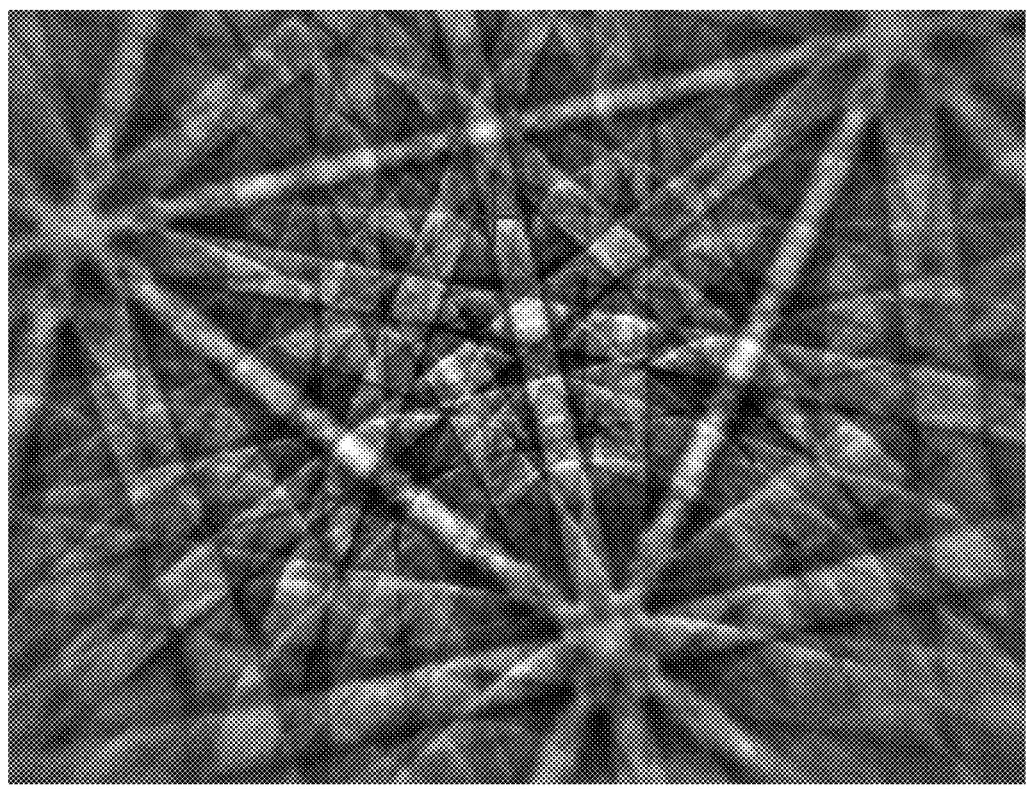
FIG. 1 illustrates an EBSD pattern and the PC of the EBSD pattern.

Step 1): collecting an EBSD pattern of a crystalline sample with an SEM, wherein FIG. 1 illustrates an EBSD pattern collected from steel, the pattern width is 151.1 mm, and the cross shown in FIG. 1 is the PC used, wherein DD=0.5886, and the accelerating voltage U used is 20 kV, wherein a wavelength of an electron beam $$\lambda = \sqrt{\frac{1.5}{U(1 + 0.9788 \times 10^{-6}U)}} = 0.008577 \text{ nm}.$$

Figure 2:
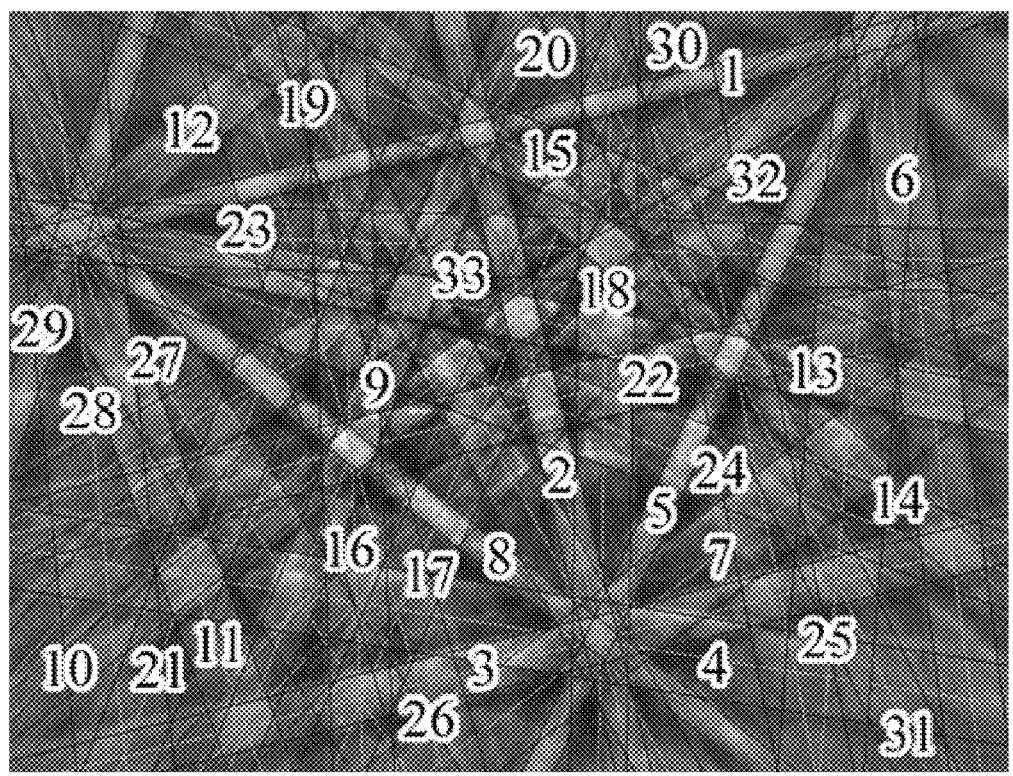
FIG. 2 illustrates the central lines and the narrowest widths of the visible Kikuchi bands in the EBSD pattern as well as the sequence numbers of the Kikuchi bands.

Step 2): FIG. 2 illustrates the detected Kikuchi bands in the EBSD pattern, wherein black parallel lines are matching with the narrowest width of the Kikuchi bands shown in the pattern, grey line between the parallel lines is the central line of the Kikuchi bands, wherein the numbers shown in FIG. 2 are sequence number of the Kikuchi bands, and the measured width of the Kikuchi bands are listed in Table 1.

Figure 3:
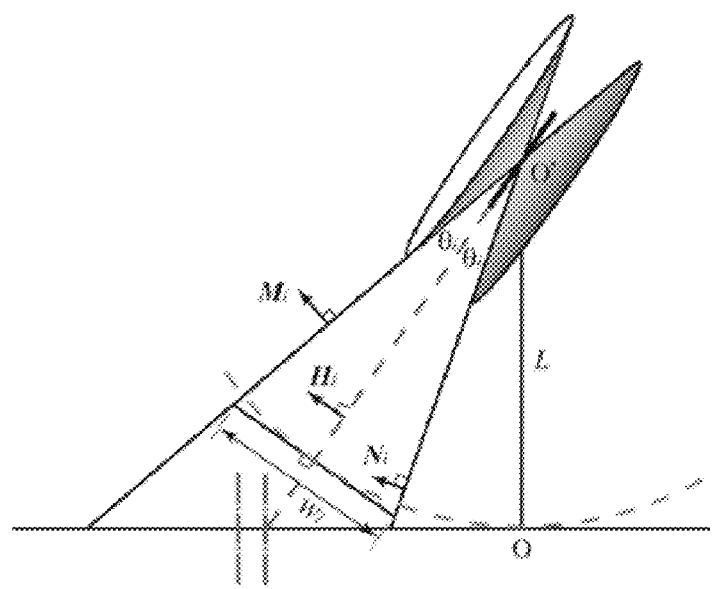
FIG. 3 is a sketch view of the formation principle of a Kikuchi band.

Step 3): FIG. 3 illustrates formation principle of a Kikuchi band, wherein the horizontal line represents an EBSD pattern plane, the intersection between two diffraction cones at the point O' and the pattern plane are the edges of the Kikuchi band; the dot dash line on the left side represents the central line of the Kikuchi band, and the dot dash line on the right side represents the trace line of the Kikuchi band; the dashed line from the point O' to the horizontal line represents a diffracting plane of the crystal, and the normal $H_i$ to the diffracting plane is directed along the direction of the reciprocal vector corresponding to the Kikuchi bands; calculating L according to the DD and the EBSD pattern width, wherein $L$=(pattern width)×DD=151.1×0.5886=88.93 mm, then determining the position of the signal source with the PC and the L, and determining the angle $2\theta_i$ between planes $M_i$ and $N_i$ according to the position of the signal source and the parallel lines, wherein the diffracting angle $\theta_i$ of the Kikuchi bands is shown in Table 1;

wherein after geometric correction, the width of the Kikuchi bands is $w_i = 2 L \tan(\theta_i)$, the length of the reciprocal vectors is $$H_i = \frac{2}{\lambda}\tan(\theta_i);$$

resolving the reciprocal vectors along the x, y and z directions of a Cartesian coordinate system, so as to obtain components (X, Y, Z), as shown in Table 1.

Step 4): selecting all possible three non-coplanar vectors in the reciprocal vectors, calculating corresponding volumes of parallelepipeds formed by the non-coplanar reciprocal vectors, wherein the volume of a parallelepiped formed by reciprocal vectors i, j and k is $V=|X_i \cdot Y_j \cdot Z_k + X_j \cdot Y_k \cdot Z_i + X_k \cdot Y_i \cdot Z_j - X_k \cdot Y_j \cdot Z_i - X_j \cdot Y_i \cdot Z_k - X_i \cdot Y_k \cdot Z_j|$ sorting the volumes from the smallest to the largest, and simultaneously recording the corresponding three non-coplanar reciprocal vectors forming the parallelepipeds, the results are listed in Table 2.

Step 5): circulating the sequenced volumes, which is started from No. 1.

Step 6): when the current V=0.7514 $nm^{-3}$, the corresponding 3D reciprocal basis consists of vectors 5, 10, and 25; all the integers I obtained from cells formed by vectors 5, 10, and any other reciprocal vector excluding vectors 5, 10, and 25 are not 2; therefore, the vectors 5, 10, and 25 are not a 3D primitive reciprocal basis; circulating to the next volume of No. 2;

when the current V=1.094 $nm^{-3}$, the corresponding 3D reciprocal basis consists of vectors 5, 7, and 19; all the integers I obtained from cells formed by vectors 5, 7, and any other reciprocal vector excluding vectors 5, 7, and 19 are not 2; therefore, the vectors 5, 7, and 19 are not a 3D primitive reciprocal basis; circulating to the next volume of No. 3;

when the current V=1.178 $nm^{-3}$, the corresponding 3D reciprocal basis consists of vectors 5, 13, and 31; the integer I obtained from the cell formed by vectors 5, 13, and 14 is 2, jumping into step 7).

Step 7): when the current V=1.178 $nm^{-3}$, the corresponding 3D reciprocal basis consists of vectors 5, 13, and 31; all the integers J obtained from cells formed by vectors 13, 31, and any other reciprocal vector excluding vectors 5, 13, and 31 are not 2; therefore, the vectors 5, 13, and 31 are not a 3D primitive reciprocal basis; circulating to the next volume of No. 4 and repeating the step 6).

In the step 6), when the current V=1.974 $nm^{-3}$, the corresponding 3D reciprocal basis consists of vectors 3, 11, and 32; all the integers I obtained from cells formed by vectors 3, 11, and any other reciprocal vector excluding vectors 3, 11, and 32 are not 2; therefore, the vectors 3, 11, and 32 are not a 3D primitive reciprocal basis; circulating to the next volume of No. 5;

when the current V=2.980 $nm^{-3}$, the corresponding 3D reciprocal basis consists of vectors 1, 19, and 21; the integer I obtained from the cell formed by vectors 1, 19, and 16 is 2, jumping into step 7).

Step 7): when the current V=2.980 $nm^{-3}$, the corresponding 3D reciprocal basis consists of vectors 1, 19, and 21; the integer J obtained from the cell formed by vectors 16, 19, and 21 is 2, jumping into step 8.

Step 8): when the current V=2.980 $nm^{-3}$, the corresponding 3D reciprocal basis consists of vectors 1, 19, and 21; all the integers K obtained from cells formed by vectors 21, 1, and any other reciprocal vector excluding vectors 1, 19, and 21 are not 2; therefore, the vectors 1, 19, and 21 are not a 3D primitive reciprocal basis; circulating to the next volume of No. 6 and repeating the step 6).

In the step 6), when the current V=4.336 $nm^{-3}$, the corresponding 3D reciprocal basis consists of vectors 5, 15, and 23; all the integers I obtained from cells formed by vectors 5, 15, and any other reciprocal vector excluding vectors 5, 15, and 23 are not 2; therefore, the vectors 5, 15, and 23 are not a 3D primitive reciprocal basis; circulating to the next volume of No. 7;

when the current V=6.475 $nm^{-3}$, the corresponding 3D reciprocal basis consists of vectors 10, 19, and 24; all the integers I obtained from cells formed by vectors 10, 19, and any other reciprocal vector excluding vectors 10, 19, and 24 are not 2; therefore, the vectors 10, 19, and 24 are not a 3D primitive reciprocal basis; circulating to the next volume of No. 8;

when the current V=6.825 $nm^{-3}$, the corresponding 3D reciprocal basis consists of vectors 12, 15, and 19; all the integers I obtained from cells formed by vectors 12, 15, and any other reciprocal vector excluding vectors 12, 15, and 19 are not 2; therefore, the vectors 12, 15, and 19 are not a 3D primitive reciprocal basis; circulating to the next volume of No. 9;

when the current V=7.636 $nm^{-3}$, the corresponding 3D reciprocal basis consists of vectors 20, 24, and 26; all the integers I obtained from cells formed by vectors 20, 24, and any other reciprocal vector excluding vectors 20, 24, and 26 are not 2; therefore, the vectors 20, 24, and 26 are not a 3D primitive reciprocal basis; circulating to the next volume of No. 10;

when the current V=11.52 nm$^{-3}$, the corresponding 3D reciprocal basis consists of vectors 19, 20, and 23; all the integers I obtained from cells formed by vectors 19, 20, and any other reciprocal vector excluding vectors 19, 20, and 23 are not 2; therefore, the vectors 19, 20, and 23 are not a 3D primitive reciprocal basis; circulating to the next volume of No. 11;

when the current V=14.75 nm$^{-3}$, the corresponding 3D reciprocal basis consists of vectors 15, 18, and 33; all the integers I obtained from cells formed by vectors 15, 18, and any other reciprocal vector excluding vectors 15, 18, and 33 are not 2; therefore, the vectors 15, 18, and 33 are not a 3D primitive reciprocal basis; circulating to the next volume of No. 12;

when the current V=57.19 nm$^{-3}$, the corresponding 3D reciprocal basis consists of vectors 4, 25, and 30; the integer I obtained from the cell formed by vectors 4, 25, and 5 is 2, jumping into step 7).

Step 7): when the current V=57.19 nm$^{-3}$, the corresponding 3D reciprocal basis consists of vectors 4, 25, and 30; the integer J obtained from the cell formed by vectors 7, 25, and 30 is 2, jumping into step 8).

Step 8): when the current V=57.19 nm$^{-3}$, the corresponding 3D reciprocal basis consists of vectors 4, 25, and 30; the integer K obtained from the cell formed by vectors 30, 4, and 5 is 2, jumping into step 9).

Step 9): determine the reciprocal vectors 4, 25 and 30 as a set of 3D primitive basis in reciprocal space.

It is clear from the embodiment that the volume of the primitive reciprocal cell is no longer unique because the measured errors are not negligible. Referring to FIG. 1, the volume of the reciprocal cells obtained from the EBSD pattern is not of distinctive discrete characteristic. As listed in Table 2, the smallest volume is 0.7514 nm$^{-3}$, and the largest one is 100.93 nm$^{-3}$. In the ranges from 0.7514 nm$^{-3}$ to 14.75 nm$^{-3}$ and from 57.19 nm$^{-3}$ to 100.93 nm$^{-3}$, there is no distinctive multiple relationship between the volumes, wherein the volumes in the above two ranges almost continuously varying, while a distinctive border exists between the two ranges. With the method given in the present invention, the volume obtained from a 3D primitive reciprocal cell should be 57.19 nm$^{-3}$, which is just at the border, wherein the volumes smaller than the value are caused by some fake cells, which are formed by the detection errors in which three Kikuchi bands belonging to the same Kikuchi pole are incorrectly detected. That is to say, three coplanar reciprocal vectors become non-coplanar and result in some fake cells. According to the preferred embodiment, the method of the present invention is able to effectively exclude fake cells. It should be noticed that the volume of the smallest non-primitive cell should be twice of that of the primitive cells, i.e. a distinctive jump should occur between 57.19 nm$^{-3}$ and 100.93 nm$^{-3}$. However, according to the preferred embodiment, the volumes almost continuously vary due to the measured errors. Continuous change in the volumes does not prevent the method of the present invention from successfully determining a real primitive reciprocal cell. The method presented in the invention is able to correctly identify one of the primitive reciprocal cells from a single EBSD pattern, and to determine a 3D primitive reciprocal basis, which is superior to the prior art.

TABLE 1 widths of the Kikuchi bands after geometric correction and corresponding reciprocal vectors

| Reciprocal vector | Width (mm) | θ (°) | X (nm$^{-1}$) | Y (nm$^{-1}$) | Z (nm$^{-1}$) |
|---|---|---|---|---|---|
| 1 | 3.755 | 1.184 | −1.118 | −4.643 | −0.6563 |
| 2 | 5.306 | 1.687 | 6.672 | −1.632 | −0.1184 |
| 3 | 7.172 | 1.479 | 1.152 | 4.681 | −3.604 |
| 4 | 12.01 | 2.627 | −1.377 | 8.715 | −6.054 |
| 5 | 4.249 | 1.125 | 3.752 | 1.733 | −1.974 |
| 6 | 9.510 | 2.048 | 6.745 | −0.8844 | −4.819 |
| 7 | 12.70 | 2.737 | 5.481 | 7.314 | −6.381 |
| 8 | 4.362 | 1.182 | −2.665 | 3.477 | −1.992 |
| 9 | 6.857 | 2.202 | −8.345 | −3.217 | −0.6235 |
| 10 | 6.138 | 1.920 | 4.750 | 6.065 | −1.326 |
| 11 | 9.263 | 2.060 | −6.544 | 2.323 | −4.706 |
| 12 | 7.531 | 2.012 | −4.861 | −5.737 | −3.250 |
| 13 | 7.082 | 2.217 | −1.670 | 8.755 | −1.445 |
| 14 | 6.362 | 2.038 | 5.447 | −6.209 | −0.7933 |
| 15 | 9.690 | 3.052 | 4.516 | −11.48 | −1.531 |
| 16 | 9.150 | 2.748 | −10.86 | 0.4040 | −2.668 |
| 17 | 9.712 | 3.091 | 11.54 | 4.809 | −1.522 |
| 18 | 8.566 | 2.638 | 10.52 | 0.1853 | −2.166 |
| 19 | 9.038 | 2.851 | −10.09 | 5.392 | −1.981 |
| 20 | 9.218 | 2.938 | −9.077 | −7.699 | −1.271 |
| 21 | 10.10 | 3.053 | −11.29 | −4.176 | −3.123 |
| 22 | 9.060 | 2.623 | 2.449 | 9.839 | −3.371 |
| 23 | 9.308 | 2.992 | −0.3807 | 12.16 | −0.6526 |
| 24 | 11.15 | 3.298 | −4.383 | 12.20 | −3.524 |
| 25 | 13.13 | 2.961 | 10.11 | 0.8506 | −6.527 |
| 26 | 12.48 | 3.620 | −13.48 | 3.825 | −4.623 |
| 27 | 13.92 | 3.232 | −9.484 | 5.958 | −6.928 |
| 28 | 14.86 | 3.204 | −10.62 | 1.060 | −7.510 |
| 29 | 4.856 | 1.102 | −3.567 | −1.121 | −2.479 |
| 30 | 11.20 | 3.199 | 12.01 | −2.375 | −4.454 |
| 31 | 8.925 | 2.682 | 9.537 | −4.479 | −2.883 |
| 32 | 10.86 | 3.235 | 9.289 | 8.617 | −3.636 |
| 33 | 10.63 | 3.401 | 6.727 | 12.08 | −0.8830 |

TABLE 2 volume of reciprocal cells and corresponding basis

| No. | Reciprocal vector | | | Volume V(nm$^{-3}$) |
|---|---|---|---|---|
| 1 | 5 | 10 | 25 | 0.7514 |
| 2 | 5 | 7 | 19 | 1.094 |
| 3 | 5 | 13 | 31 | 1.178 |
| 4 | 3 | 11 | 32 | 1.974 |
| 5 | 1 | 19 | 21 | 2.980 |
| 6 | 5 | 15 | 23 | 4.336 |
| 7 | 10 | 19 | 24 | 6.475 |
| 8 | 12 | 15 | 19 | 6.825 |
| 9 | 20 | 24 | 26 | 7.636 |
| 10 | 19 | 20 | 23 | 11.52 |
| 11 | 15 | 18 | 33 | 14.75 |
| 12 | 4 | 25 | 30 | 57.19 |
| 13 | 5 | 23 | 30 | 61.06 |
| 14 | 15 | 23 | 25 | 62.90 |
| 15 | 3 | 7 | 30 | 64.03 |
| 16 | 10 | 30 | 33 | 65.43 |
| 17 | 3 | 17 | 26 | 65.81 |
| 18 | 10 | 17 | 23 | 66.22 |
| 19 | 10 | 15 | 30 | 67.40 |
| 20 | 21 | 23 | 26 | 69.77 |
| 21 | 1 | 17 | 30 | 69.79 |
| 22 | 10 | 20 | 28 | 70.64 |
| 23 | 24 | 30 | 31 | 71.60 |
| 24 | 23 | 30 | 32 | 71.74 |
| 25 | 14 | 23 | 32 | 71.82 |
| 26 | 3 | 28 | 32 | 71.91 |
| 27 | 6 | 20 | 25 | 72.11 |
| 28 | 2 | 17 | 23 | 72.55 |
| 29 | 10 | 21 | 27 | 72.76 |
| 30 | 7 | 24 | 30 | 72.94 |

TABLE 2-continued volume of reciprocal cells and corresponding basis

| No. | Reciprocal vector | | | Volume V(nm⁻³) |
|---|---|---|---|---|
| 31 | 4 | 6 | 31 | 73.00 |
| 32 | 16 | 21 | 23 | 74.16 |
| 33 | 15 | 17 | 18 | 74.51 |
| 34 | 14 | 18 | 33 | 74.55 |
| 35 | 10 | 22 | 27 | 74.60 |
| 36 | 12 | 14 | 21 | 74.62 |
| 37 | 13 | 14 | 25 | 74.83 |
| 38 | 7 | 26 | 27 | 75.51 |
| 39 | 2 | 19 | 25 | 75.88 |
| 40 | 17 | 23 | 33 | 75.90 |
| 41 | 17 | 22 | 24 | 76.00 |
| 42 | 14 | 31 | 32 | 76.82 |
| 43 | 24 | 25 | 31 | 76.89 |
| 44 | 8 | 17 | 22 | 77.15 |
| 45 | 18 | 22 | 32 | 77.25 |
| 46 | 5 | 15 | 32 | 77.38 |
| 47 | 20 | 22 | 27 | 77.51 |
| 48 | 5 | 18 | 24 | 77.68 |
| 49 | 16 | 20 | 23 | 77.68 |
| 50 | 9 | 19 | 23 | 77.72 |
| 51 | 12 | 15 | 26 | 77.77 |
| 52 | 15 | 31 | 33 | 78.60 |
| 53 | 7 | 24 | 25 | 78.90 |
| 54 | 4 | 22 | 28 | 79.35 |
| 55 | 8 | 21 | 24 | 79.43 |
| 56 | 1 | 12 | 26 | 79.69 |
| 57 | 14 | 15 | 17 | 80.03 |
| 58 | 20 | 21 | 24 | 80.27 |
| 59 | 18 | 20 | 31 | 80.49 |
| 60 | 13 | 18 | 22 | 80.61 |
| 61 | 4 | 26 | 32 | 81.16 |
| 62 | 9 | 10 | 24 | 81.91 |
| 63 | 17 | 19 | 24 | 82.04 |
| 64 | 17 | 19 | 24 | 82.04 |
| 65 | 21 | 28 | 32 | 82.18 |
| 66 | 10 | 13 | 19 | 82.19 |
| 67 | 10 | 13 | 19 | 82.19 |
| 68 | 1 | 19 | 20 | 82.33 |
| 69 | 1 | 19 | 20 | 82.33 |
| 70 | 28 | 29 | 33 | 82.66 |
| 71 | 15 | 16 | 19 | 82.74 |
| 72 | 15 | 16 | 19 | 82.74 |
| 73 | 9 | 20 | 23 | 82.78 |
| 74 | 12 | 15 | 16 | 83.03 |
| 75 | 14 | 15 | 21 | 83.40 |
| 76 | 13 | 23 | 26 | 83.45 |
| 77 | 4 | 14 | 24 | 83.55 |
| 78 | 4 | 14 | 24 | 83.55 |
| 79 | 4 | 27 | 32 | 83.86 |
| 80 | 16 | 26 | 33 | 84.30 |
| 81 | 16 | 26 | 33 | 84.30 |
| 82 | 4 | 9 | 11 | 84.64 |
| 83 | 4 | 16 | 17 | 84.72 |
| 84 | 4 | 9 | 16 | 84.82 |
| 85 | 4 | 9 | 16 | 84.82 |
| 86 | 13 | 20 | 26 | 84.84 |
| 87 | 13 | 20 | 26 | 84.84 |
| 88 | 20 | 22 | 28 | 84.87 |
| 89 | 9 | 10 | 27 | 84.91 |
| 90 | 14 | 18 | 32 | 85.25 |
| 91 | 2 | 9 | 23 | 85.28 |
| 92 | 2 | 17 | 24 | 85.50 |
| 93 | 17 | 19 | 32 | 85.58 |
| 94 | 17 | 19 | 32 | 85.58 |
| 95 | 9 | 20 | 31 | 85.67 |
| 96 | 18 | 22 | 24 | 85.74 |
| 97 | 16 | 26 | 32 | 85.89 |
| 98 | 9 | 27 | 32 | 86.11 |
| 99 | 9 | 27 | 32 | 86.11 |
| 100 | 2 | 13 | 32 | 86.18 |
| 101 | 2 | 13 | 32 | 86.18 |
| 102 | 8 | 15 | 27 | 86.29 |
| 103 | 8 | 15 | 27 | 86.29 |
| 104 | 8 | 26 | 33 | 86.32 |
| 105 | 19 | 22 | 32 | 86.41 |
| 106 | 8 | 26 | 32 | 86.65 |
| 107 | 1 | 7 | 33 | 86.71 |
| 108 | 1 | 7 | 33 | 86.71 |
| 109 | 11 | 27 | 33 | 86.77 |
| 110 | 11 | 27 | 33 | 86.77 |
| 111 | 22 | 28 | 33 | 87.15 |
| 112 | 16 | 27 | 32 | 87.29 |
| 113 | 16 | 27 | 32 | 87.29 |
| 114 | 17 | 26 | 32 | 87.81 |
| 115 | 8 | 19 | 32 | 88.19 |
| 116 | 8 | 19 | 32 | 88.19 |
| 117 | 16 | 20 | 24 | 88.28 |
| 118 | 2 | 14 | 33 | 88.65 |
| 119 | 6 | 7 | 15 | 89.25 |
| 120 | 11 | 28 | 33 | 89.38 |
| 121 | 11 | 28 | 33 | 89.38 |
| 122 | 21 | 24 | 26 | 90.31 |
| 123 | 24 | 26 | 33 | 90.34 |
| 124 | 24 | 26 | 33 | 90.34 |
| 125 | 18 | 31 | 33 | 91.34 |
| 126 | 20 | 27 | 33 | 92.08 |
| 127 | 20 | 27 | 33 | 92.08 |
| 128 | 9 | 24 | 33 | 92.42 |
| 129 | 9 | 24 | 33 | 92.42 |
| 130 | 2 | 13 | 33 | 92.53 |
| 131 | 9 | 16 | 24 | 92.78 |
| 132 | 20 | 26 | 33 | 94.44 |
| 133 | 15 | 31 | 32 | 94.49 |
| 134 | 7 | 16 | 27 | 95.04 |
| 135 | 15 | 17 | 33 | 99.40 |
| 136 | 13 | 16 | 33 | 100.80 |
| 137 | 13 | 19 | 20 | 100.93 |

The preferred embodiment has been shown and described for the purposes of illustrating the functional and structural principles of the present invention and is subject to change without departure from such principles. Therefore, this invention includes all modifications encompassed within the spirit and scope of the following claims.

What is claimed is:

1. A method for determining a 3D primitive reciprocal basis of an unknown crystal based on an EBSD pattern, comprising steps of:
   1) collecting an electron backscatter diffraction (EBSD) pattern of a crystalline sample with a scanning electron microscope (SEM), recording the pattern center (PC), the detector distance (DD), and the accelerating voltage used;
   2) identifying edges at the narrowest width of each visible Kikuchi band on the EBSD pattern, determining central line of the Kikuchi bands on the EBSD pattern;
   3) geometrically correcting the Kikuchi bands with the pattern center and the detector distance, obtaining reciprocal vectors corresponding to the Kikuchi bands, and determining components of the reciprocal vectors in a 3D reciprocal Cartesian coordinate system;
   4) selecting all possible three non-coplanar vectors in the reciprocal vectors, calculating the volumes of parallelepipeds defined by the non-coplanar reciprocal vectors, sequencing them from the smallest volume to the largest volume, and simultaneously recording the corresponding three non-coplanar reciprocal vectors forming the parallelepipeds;
   5) circulating the sequenced volumes;
   6) assigning the current volume to be variable V, wherein the three corresponding non-coplanar reciprocal vectors are respectively set to be a, b, and c, firstly calculating the parallelepiped volumes $V_{ab}$ formed by the a, b, and another reciprocal vector excluding the a, b, and c, then calculating $V_{ab}/V$, taking the nearest integers I; if one of the integers I equals to 2, jumping into step 7); otherwise, circulating to the next volume and repeating the step 6);

7) firstly calculating the parallelepiped volumes $V_{bc}$ formed by b, c, and another reciprocal vector excluding the a, b, and c, then calculating $V_{bc}/V$, taking the nearest integers J; if one of the integers J equals to 2, jumping into step 8); otherwise, circulating to the next volume and repeating the step 6);

8) firstly calculating the parallelepiped volumes $V_{ca}$ formed by c, a, and another reciprocal vector excluding the a, b, and c, then calculating $V_{ca}/V$, taking the nearest integers K; if one of the integers K equals to 2, jumping into step 9); otherwise, circulating to the next volume and repeating the step 6); and 9) determining the three non-coplanar reciprocal vectors corresponding to the current volume as a 3D primitive reciprocal basis.

2. The method, as recited in claim 1, wherein in the step 2), firstly determining the central line of the Kikuchi bands, then matching the edges at the narrowest width of the Kikuchi bands with symmetrical parallel lines, so as to represent the width of the Kikuchi bands.

3. The method, as recited in claim 1, wherein in the step 2), matching the edges at the narrowest width of the Kikuchi bands with a pair of parallel lines, representing the width of the Kikuchi bands with the interval between the parallel lines, and representing the central line of the Kikuchi bands with the bisector of the parallel lines.

4. The method, as recited in claim 1, wherein the step 3) specifically comprises sub-steps of:

3-1) calculating L according to the DD and the EBSD pattern width, wherein $L=$(pattern width)$\times$DD, wherein the L is a distance from the signal source to the PC of the EBSD pattern;

3-2) determining a position of the signal source with the PC and the L;

3-3) determining the angle $2\theta_i$ between planes $M_i$ and $N_i$ according to the position of the signal source and the parallel lines at the narrowest width of the Kikuchi bands, wherein after geometric correction, the width of the Kikuchi bands is $w_i = 2L\tan(\theta_i)$, the length of the reciprocal vectors is $$H_i = \frac{2}{\lambda}\tan(\theta_i);$$

and 3-4) determining the trace line of the Kikuchi bands with the intersection line formed by a bisector of planes $M_i$ and $N_i$ and the EBSD pattern plane.

* * * * *